(12) United States Patent
Lechsel et al.

(10) Patent No.: US 8,515,003 B2
(45) Date of Patent: Aug. 20, 2013

(54) DETERMINING A PHASE OF AN OBJECT MOVEMENT IN A SERIES OF IMAGES

(75) Inventors: Gerhard Lechsel, Erlangen (DE); Andreas Rau, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 118 days.

(21) Appl. No.: 13/179,002

(22) Filed: Jul. 8, 2011

(65) Prior Publication Data
US 2012/0008737 A1 Jan. 12, 2012

(30) Foreign Application Priority Data
Jul. 9, 2010 (DE) .......... 10 2010 026 675

(51) Int. Cl.
*A61B 6/00* (2006.01)
(52) U.S. Cl.
USPC .............................. 378/8; 378/4; 378/42
(58) Field of Classification Search
USPC ............................ 378/8, 42; 382/128, 131
See application file for complete search history.

(56) References Cited

U.S. PATENT DOCUMENTS

| | | | | |
|---|---|---|---|---|
| 6,421,552 | B1 * | 7/2002 | Hsieh ............................ | 600/425 |
| 7,349,564 | B2 | 3/2008 | Zijp et al. | |
| 2002/0025017 | A1 * | 2/2002 | Stergiopoulos et al. .......... | 378/8 |
| 2003/0123604 | A1 * | 7/2003 | Edic et al. ....................... | 378/19 |
| 2004/0136490 | A1 | 7/2004 | Edic et al. | |
| 2004/0165695 | A1 * | 8/2004 | Karimi et al. ................... | 378/19 |
| 2004/0234115 | A1 | 11/2004 | Zijp et al. | |
| 2006/0109952 | A1 * | 5/2006 | Chen ............................... | 378/4 |
| 2006/0193429 | A1 * | 8/2006 | Chen ............................... | 378/4 |
| 2007/0030946 | A1 * | 2/2007 | Tsuyuki et al. ................... | 378/8 |
| 2008/0025588 | A1 * | 1/2008 | Zhang et al. ................... | 382/130 |
| 2010/0074490 | A1 * | 3/2010 | Arakita et al. ................ | 382/128 |

FOREIGN PATENT DOCUMENTS
WO WO 2004/054443 A1 7/2004

OTHER PUBLICATIONS

German Office Action dated Apr. 4, 2011 for corresponding German Patent Application No. DE 10 2010 026 675.2-35 with English translation.

Dietrich L. et al., "Linac-integrated 4D cone beam CT: first experimental results," Physics in Medicine and Biology 51 (2006): pp. 2939-2952.

Sugimoto N. et al., "Medical Image Processing in Collaboration with Medical Researchers," Second International Conference on Informatics Research for Development of Knowledge Society Infrastructure (2007): pp. 77-86.

Sonke J. J. et al., "Respiratory correlated cone beam CT," Medical Physics 32 (4), (2005), pp. 1176-1186.

* cited by examiner

*Primary Examiner* — Alexander H Taningco
(74) *Attorney, Agent, or Firm* — Lempia Summerfield Katz LLC

(57) ABSTRACT

A method for determining a movement phase of a periodically moving object in a plurality of sequentially produced images in a series of images of the periodically moving object. The method includes registering different images in the series of images. The method also includes determining a deformation that has occurred between the registered images. The method further includes—determining the phase of the movement of the moving object for at least one of the images in the series of images based upon the determined deformation.

25 Claims, 5 Drawing Sheets

DETERMINING A PHASE OF AN OBJECT MOVEMENT IN A SERIES OF IMAGES

This application claims the benefit of DE 10 2010 026 675.2, filed Jul. 9, 2010.

BACKGROUND

The present embodiments relate to an apparatus, medical imaging device, computer program product and/or a method for determining a movement phase of a moving object shown in a series of images. For example, methods and apparatuses of this type are used in medical imaging, since a reconstruction of three-dimensional images depends on the movement phase of the moving object (e.g., a lung) occurring while raw image data is being recorded.

Cone beam computed tomography is an example of a known medical imaging method. Cone beam computed tomography produces two-dimensional projections of the object using x-ray beams. The projections are produced using different angles from an angle range of over 180°. A three-dimensional image of the object may then be reconstructed from the two-dimensional projections.

Producing all of these two-dimensional projections from different directions is a time-consuming process. If the object (e.g., lung) to be imaged moves during this time (e.g., the lung executes a quasi-periodic, respiratory, movement), the individual projection image data items are produced in different phases of the object movement. If the projections are then used to reconstruct a three-dimensional image, the inconsistent projections may produce artifacts. Artifacts make it difficult to evaluate and/or diagnose the three-dimensional image.

One way of preventing such artifacts is only to use projections that correspond to the same respective movement phase of the moving object. For example, only projection images that correspond to the same respiratory position may be used for the reconstruction.

One way of determining the respiratory position is to use a respiration strap, as described in: Lars Dietrich et al, "Linac-integrated 4D cone beam CT: first experimental results," 2006, Phys. Med. Biol. 51, 2939.

U.S. Pat. No. 7,349,564 discloses a method for determining the respiratory position of anatomical features, such as, for example, a diaphragm, in the image data.

SUMMARY AND DESCRIPTION

The present embodiments may obviate one or more of the drawbacks or limitations in the related art. For example, a method, imaging device, computer program product and/or apparatus for determining, robustly and without external aids, a movement phase of a moving object in a series of images, may be provided.

A method for determining a movement phase of a periodically moving object in a plurality of sequentially produced images of a series of images of the moving object may comprise the following acts: (1) registering different images in the series of images with one another such that a deformation (e.g., displacement), representative of a measure of the change that has occurred between the registered images, is determined, and (2) using the deformation or displacement to determine the movement phase of the moving object for at least one of the plurality of sequentially produced images in the series of images.

It is advantageous to determine the movement phase of the moving object for individual images in the series of images using only the images themselves. However, this may be problematic if a determination is made on an anatomical feature, such as, for example, the diaphragm, considered in isolation in the image data.

In one embodiment, the movement phase of the moving object movement is based upon a registration performed between different images in the series of images.

Such a registration permits a deformation or displacement, which is a measure of how the object has changed between the two images being registered, to be determined. A displacement may, for example, be determined by registration. The deformation established by registration may be used to derive or determine the movement phase of the moving object for one and/or for several images in the series of images.

Advantageously, registration between the images may be continuously performed. As a result, the method is less sensitive, in that not all of the relevant anatomical features, on which a feature-based phase determination is normally based, have to be visible or detectable in individual images. Determination of the phase of the moving object is therefore possible even if the anatomical feature is not visible or cannot be detected in all of the projections.

Registration may, for example, be a linear registration, which determines the deformation between two images. In one embodiment, the two images are consecutive images in the series of images. Based on the extent of the deformation, a displacement and, more particularly, a displacement vector or length, may be determined.

Registration does not have to be applied to the entire image content of the images, as it may, for example, be sufficient to define a subregion of the images and apply the registration to that subregion. The subregion, may, for example, be selected by a user input.

The registration may be applied to any two consecutive images such that each image of the two consecutive images is registered with the other image of the two consecutive images. The deformation, which is a measure of the change that occurs between consecutive images, may then be determined.

Accordingly, the phase position for one or more of the images in the series of images may be determined. For example, the respiratory position or the time point in the cardiac cycle may be determined from the image when recorded.

The images in the series of images may be a series of sequential fluoroscopy images produced using, for example, x-ray beams, for an object to be examined. In one embodiment, the fluoroscopy images may be cone beam computed tomography projections.

Advantageously, the disclosed method reduces or minimizes the likelihood that the phase of the moving object in a cone beam computed tomography will be incorrectly determined and, thus, lead to an artifact-prone reconstruction. Because the projections may be produced from a plurality of different directions, the position of an anatomical feature in the projections may change significantly or even "slip" out of individual projections. Feature-based phase determinations are thus problematic and/or error-prone.

With cone beam computed tomography, it is possible to use, for example, an eccentric projection geometry, in which the center of rotation of the CBCT does not lie symmetrically in the x-ray cone beam emitted for fluoroscopy purposes. The x-ray cone beam may be deflected in an oblique direction, to the side of the center, to strike a laterally offset, eccentric detector.

Because of the eccentric projection geometry, it is easy for an anatomical feature to change position as a function of the projection angle or even to be blocked out. Therefore, when used in connection with an eccentric projection geometry, the disclosed registration-based method avoids the disadvantages of a feature-based reconstruction and other simple threshold value methods that might produce incorrect results.

Advantageously, the movement phase of the moving object may be determined from a few consecutive images. Thus, the phase position of the moving object may be correctly determined without having to wait for a complete movement period of the moving object.

From the deformations or displacements that occur and are measured between images in the series of images, it is possible to form a signal that may then be used to determine the phase.

The signal is, therefore, indicative of how much the images in the series of images have changed, been deformed, or been displaced, relative to one another, during the series of images. For example, the signal may be generated by adding the displacements that have occurred between consecutive images in the series of images.

The phase of the moving object may be determined using the signal. For example, a Hilbert transformation may be applied to the signal. The Hilbert transformation may be considered to be a phase displacement through 90° in the frequency space.

The movement phase of the moving object may be determined for individual, several, or even all of the images in the series of images. All of the images in the series of images may thus be classified by, for example, sorting the images according to the movement phase of the moving object assigned to them.

Consequently, only images having the movement phase of the moving object that lies within a certain interval may be used for a subsequent reconstruction. In turn, the reconstructed image will have fewer movement-induced artifacts.

An apparatus that evaluates a series of images of a periodically moving object to determine a phase of movement of the periodically moving object may be provided. The series of images includes a plurality of sequentially produced images of the periodically moving object. The apparatus comprises a computer unit that is configured to: (1) register different images in the series of images; (2) determine a deformation, or a change that has occurred, between the registered images; and (3) determine a movement phase of the moving object for at least one of the images in the series of images using the determined deformation.

In one embodiment, the disclosed methods may be implemented in the computer unit.

In one embodiment, the disclosed apparatus may be used in connection with an imaging device that includes an x-ray beam source and an x-ray detector configured to produce the series of images of an object.

In one embodiment, a non-transitory computer readable program or medium may have machine-readable instructions executable on a computer unit stored thereon. The machine-readable instructions may implement the disclosed method.

DETAILED DESCRIPTION OF THE DRAWINGS

Figure 1:
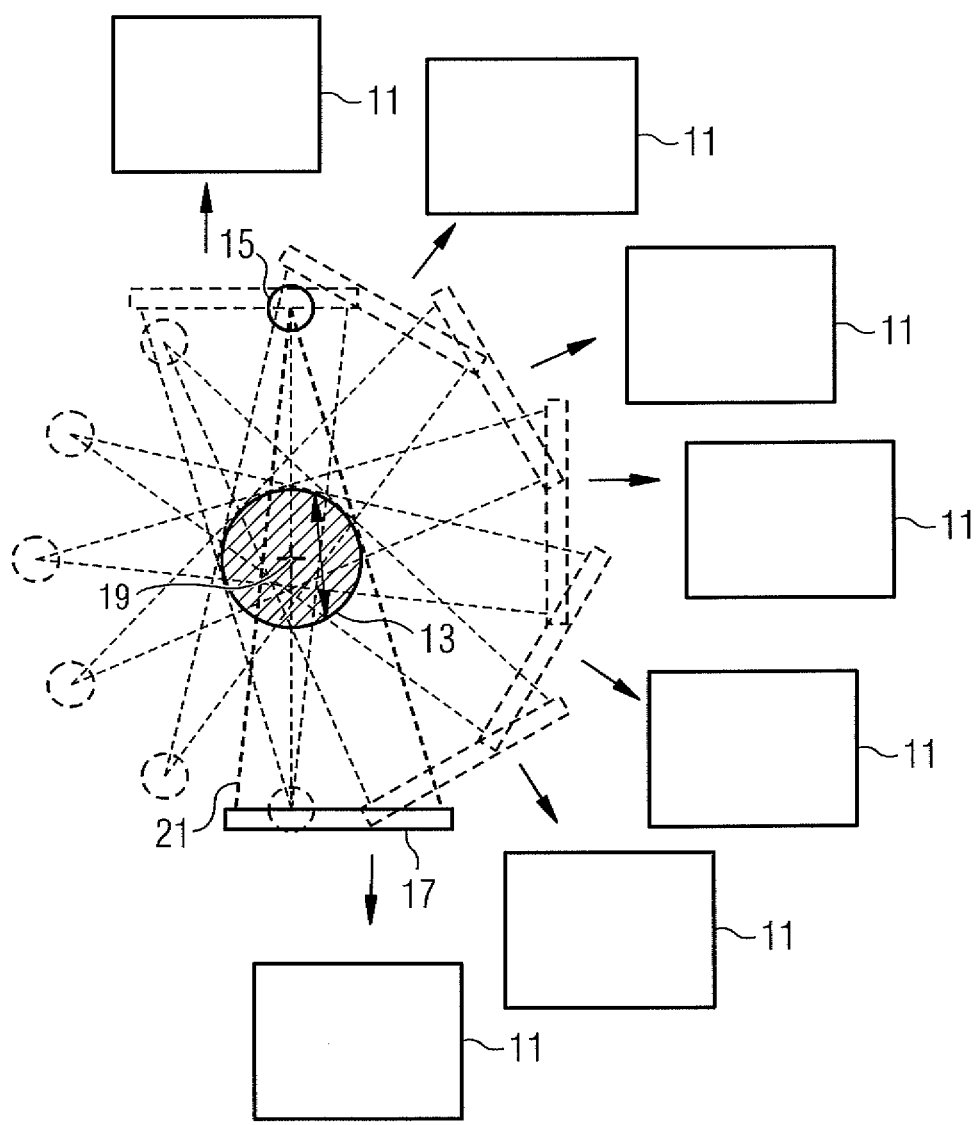
FIG. 1 shows a schematic diagram of a cone beam computed tomograph with eccentric projection geometry.

FIG. 1 shows a schematic diagram of cone beam computed tomography that is used to produce projection images 11 of an object 13 to be examined.

An x-ray source 15 and an x-ray detector 17 rotate about a common center of rotation 19. The x-ray source 15 directs an x-ray cone beam 21 onto the x-ray detector 17. The x-ray detector 17 is in an eccentric position such that the center of rotation 19 does not lie centrally in the x-ray cone beam 21.

A plurality of projection images 11 are successively produced by rotating the x-ray source 15 and x-ray detector 17. The plurality of projection images 11 form a series of images of the object 13 to be examined.

Because of a movement of the object 13, which is shown by the arrow in FIG. 1, the object may have one movement phase in one projection image and a different movement phase in another projection image. When performing reconstruction, however, it is advantageous to use projection images in which the object 13 had a similar movement phase.

With reference to FIGS. 2 through 5, registration may be used to determine the movement phase of the moving object during the production of a projection image.

Figure 2:
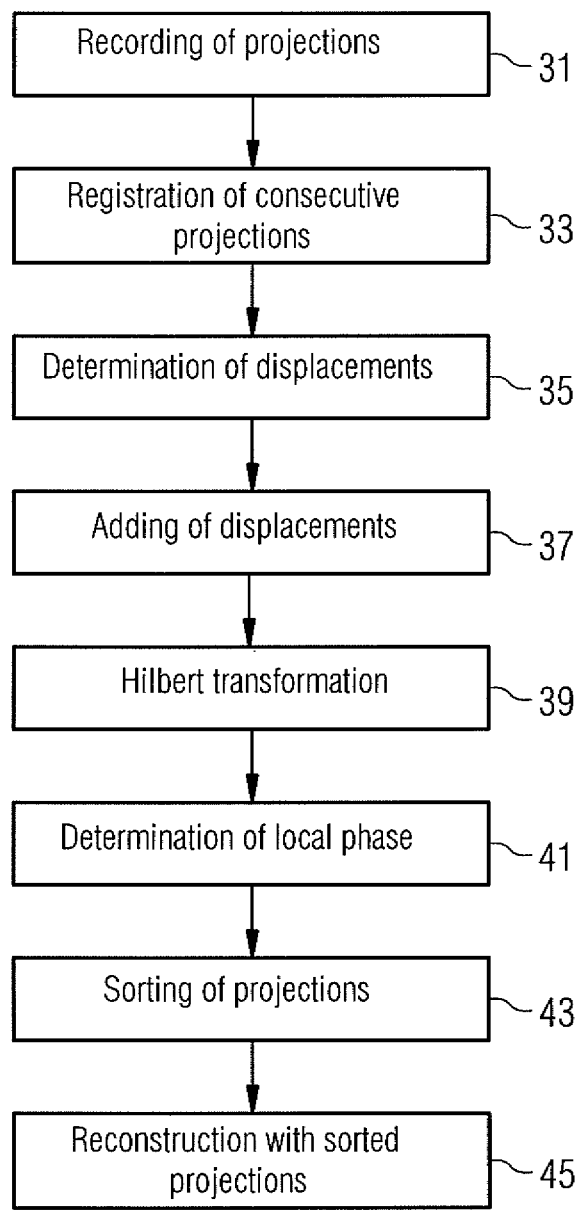
FIG. 2 shows a flow diagram of one embodiment of a method for determining a movement phase of a moving object.

FIG. 2 shows a flow diagram for one embodiment of a method for determining a movement phase of a moving object. In act 31, the projection images are recorded. In act 33, any of two consecutive projection images are registered with one another. Registration establishes how much the object to be examined has been displaced between one projection image and the next projection image. This may be done, for example, by optimizing the summed squared difference of the image gray-scale values along a predefined axis such as, for example, a body axis (e.g., a longitudinal body axis). In other embodiments, linear registration may also be used.

In act 35, the displacement between each of the two consecutive projection images may be determined. In act 37, the displacements determined in act 35 are successively added. In turn, a signal indicative of how the object to be examined has been displaced throughout the series of images may be generated.

In a pre-processing step, a frequency filter may be applied to this signal. Smoothing and/or edge filters, or a combination of the two filters, may be used to suppress signal frequencies that deviate too much from, for example, a normal respiratory frequency.

In act 39, this preprocessed signal is subjected to an applied discrete Hilbert transformation. In act 41, the signal and the Hilbert-transformed portion of the signal may be used to assign a local phase to each projection image.

If s(p) represents the signal (p for projection image number), an analytical signal $f(p)$ may be obtained by applying $f(p)=s(p)+i\ Hs(p)$, where Hs(p) is the Hilbert-transformed portion of s(p). The complex function $f(p)$ may, alternatively, be written as $f(p)=F(p)\cdot\exp(i\ ph(p))$, where ph(p) is the local phase. The local phase may be assigned to the individual projections.

In act 43, the projection images may be classified based on or according to the local phase. A subsequent image reconstruction may be performed using the classified projection images (act 45).

Figure 3:
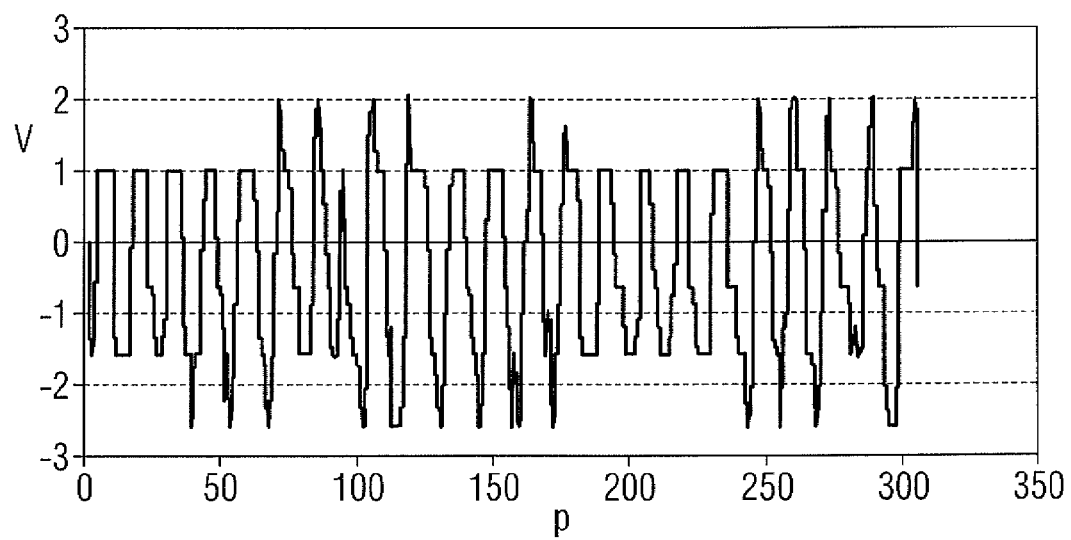
FIG. 3 shows a displacement that occurs between each two consecutive images over a series of images.

FIG. 3 illustrates the displacement V that occurs between two projection images as a function of the projection image number p.

Figure 4:
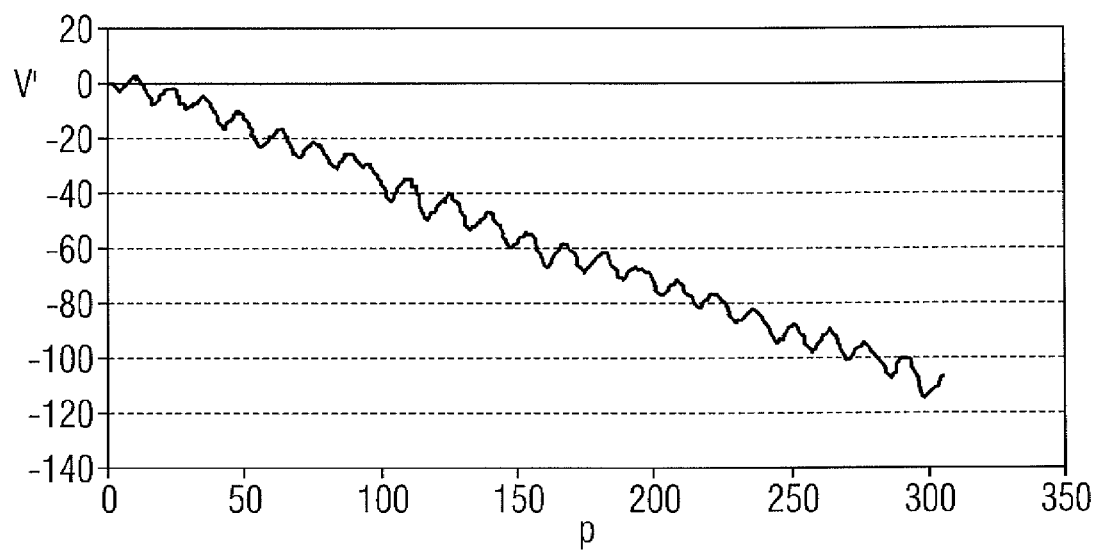
FIG. 4 shows a signal generated by adding the displacements.

In FIG. 4, the summed displacements V' are plotted as a function of the projection image number p. A projection image number is assigned to the sum of all the displacements that have already occurred.

Figure 5:
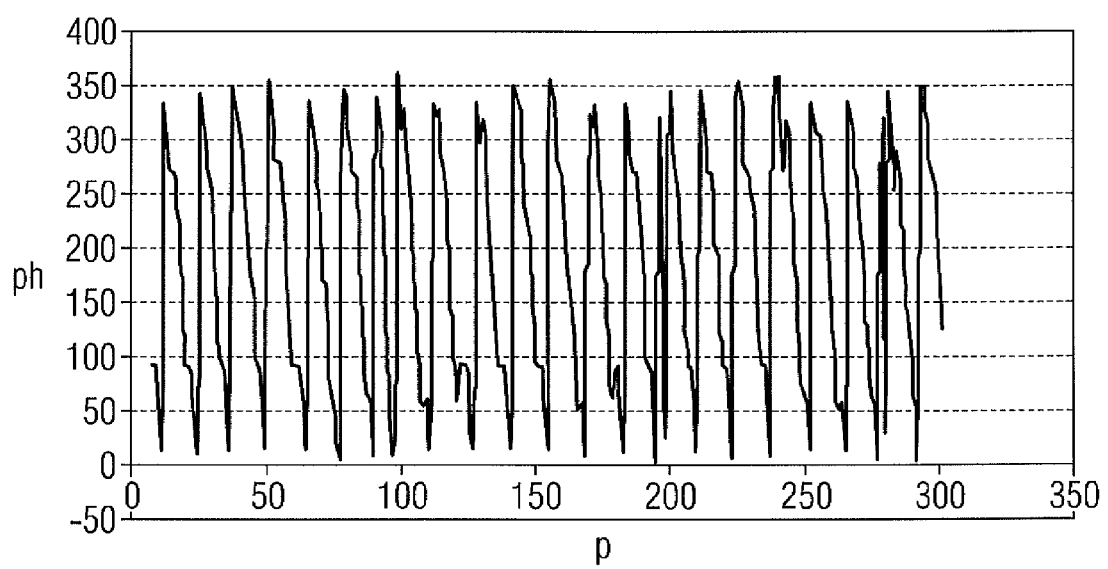
FIG. 5 shows a local phase determined by applying a Hilbert transformation to the signal for the individual images in the series of images.

FIG. 5 shows a plot of the local phase ph, which may be determined for each projection image using the Hilbert transformation, as a function of the projection image number p. The local phase may be used to robustly assign a projection image to a movement phase of the moving object, such as, for example, a respiratory position.

Figure 6:
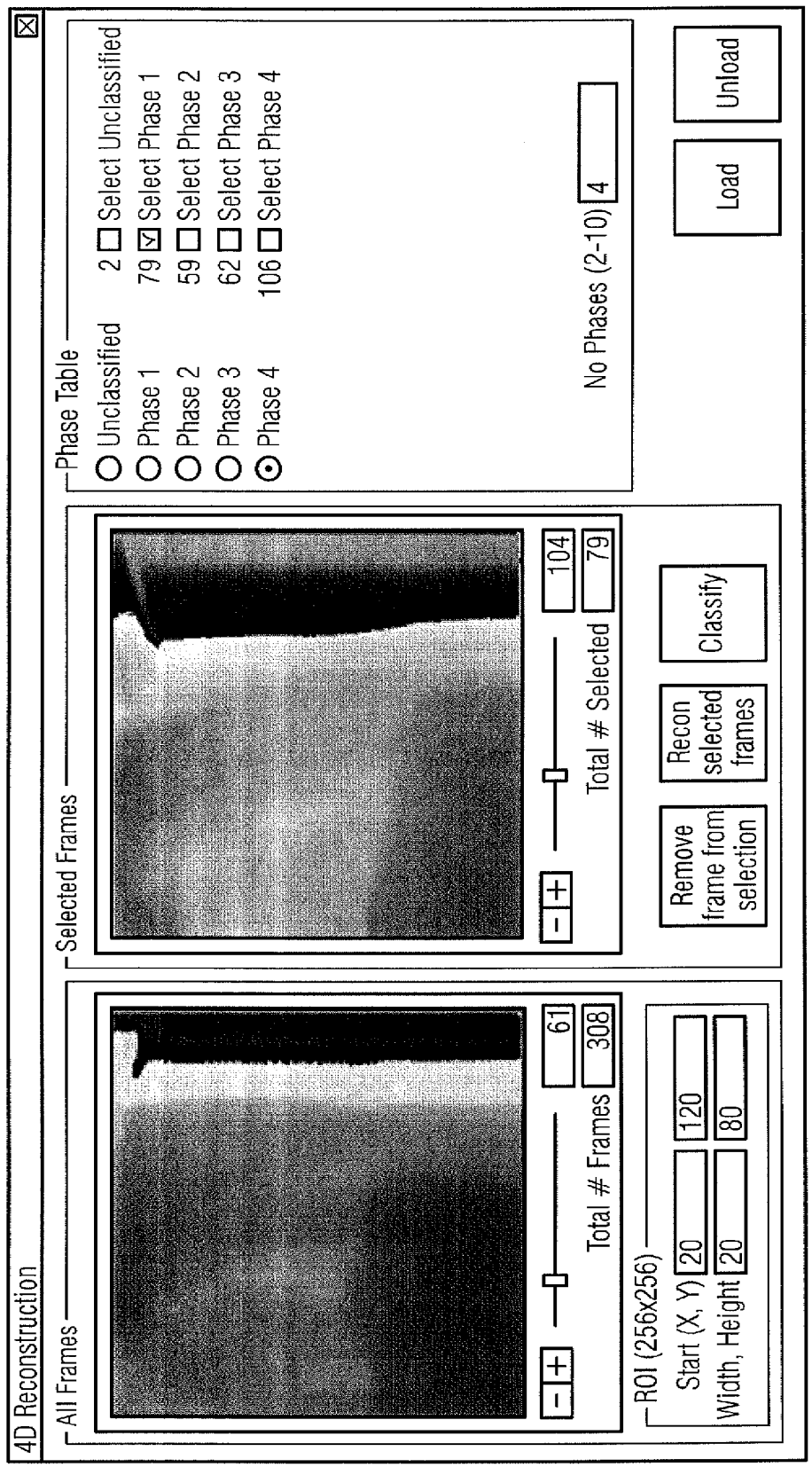
FIG. 6 shows a diagram of a graphical user interface that may be used to input settings for the method shown in FIG. 1.

FIG. 6 shows a diagram of a graphical user interface that may be used to input and receive the settings for the disclosed method.

The left-hand third of the figure, labeled 61, shows all of the projection images. A user may also set the region of interest ROI to be used as the basis for the registration algorithm.

In the right-hand third of the figure, labeled 63, the number of phase positions of a movement cycle into which the projection images are to be sorted or classified may be set. The number of projection images present for each of the phase positions is indicated. A user may also select the phase position.

In the center third of the figure, labeled 65, the projection images of the selected phase position may be displayed. A reconstruction may be performed using the classified projection images.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a movement phase of a periodically moving object, the method comprising:
   providing a plurality of sequentially produced images in a series of images of the moving object;
   registering, via a computer unit, different images in the series of images;
   determining, via the computer unit, a deformation that has occurred between the registered images;
   forming, via the computer unit, a signal indicative of the deformation between the registered images; and
   determining, via the computer unit, the movement phase of the moving object for at least one of the plurality of sequentially produced images in the series of images using a Hilbert transformation on the signal.

2. The method as claimed in claim 1, wherein determining the deformation comprises determining a displacement that has occurred between the registered images.

3. The method as claimed in claim 1, wherein providing the plurality of sequentially produced images comprises providing a series of sequentially produced fluoroscopy images of the moving object.

4. The method as claimed in claim 3, wherein providing the series of sequentially produced fluoroscopy images comprises providing cone beam computed tomography projections produced with an eccentric projection geometry.

5. The method as claimed in claim 4, wherein registering comprises registering two consecutive images in the series of images, and wherein determining the deformation comprises determining the deformation that has occurred between the two consecutive images.

6. The method as claimed in claim 5, wherein forming the signal comprises forming the signal by adding consecutive deformations.

7. The method as claimed in claim 6, wherein determining the phase comprises determining the movement phase of the moving object for each of the plurality of sequentially produced images in the series of images.

8. The method as claimed in claim 7, further comprising classifying each of the plurality of sequentially produced images according to the phase assigned to a respective image of the plurality of sequentially produced images.

9. The method as claimed in claim 8, further comprising performing an image reconstruction using only images of the plurality of sequentially produced images having the phase that lies within a certain interval.

10. The method as claimed in claim 1, wherein registering comprises registering two consecutive images in the series of images, and wherein determining the deformation comprises determining the deformation that has occurred between the two consecutive images.

11. The method as claimed in claim 1, wherein forming the signal comprises forming the signal by adding consecutive deformations.

12. The method as claimed in claim 1, wherein determining the phase comprises determining the movement phase of the moving object for each of the plurality of sequentially produced images in the series of images.

13. The method as claimed in claim 12, further comprising classifying each of the plurality of sequentially produced images according to the phase assigned to a respective image of the plurality of sequentially produced images.

14. The method as claimed in claim 13, further comprising performing an image reconstruction using only images of the plurality of sequentially produced images having the phase that lies within a certain interval.

15. The method as claimed in claim 1, further comprising:
   assigning the determined movement phase to images in the series of images; and
   reconstructing an image of the moving object based on the assigning.

16. The method as claimed in claim 1, further comprising applying the Hilbert transformation on the signal, wherein determining the movement phase comprises determining the movement phase based on the applying.

17. An apparatus configured to evaluate a plurality of sequentially produced images in a series of images of an object to determine a movement phase of the object, the apparatus comprising a computer unit configured to:
   register different images in the series of images;
   determine a displacement that has occurred between the registered images;
   form a signal indicative of the displacement between the registered images; and
   determine the movement phase of the object for at least one of the plurality of sequentially produced images in the series of images by applying a Hilbert transformation to the signal.

18. The apparatus as claimed in claim 17, wherein the signal is formed by adding consecutive displacements.

19. The apparatus as claimed in claim 17, wherein the computer unit is configured to determine the movement phase of the object for each of the plurality of sequentially produced images in the series of images.

20. The apparatus as claimed in claim 19, wherein the computer unit is configured to classify each of the plurality of sequentially produced images according to the phase assigned to a respective image of the plurality of sequentially produced images.

21. The apparatus as claimed in claim 20, wherein the computer unit is configured to perform an image reconstruction using only images of the plurality of sequentially produced images having the phase that lies within a certain interval.

22. The apparatus as claimed in claim 17, wherein the computer unit is further configured to:
   assign the determined movement phase to images in the series of images; and
   reconstruct an image of the object based on the assignment of the determined movement phase.

23. An imaging device for imaging an object, the imaging device comprising:
   an apparatus configured to evaluate a plurality of sequentially produced images in a series of images of an object to determine a movement phase of the object, the apparatus comprising a computer unit configured to:
   register different images in the series of images;
   determine a displacement that has occurred between the registered images;
   form a signal indicative of the displacement between the registered images; and
   determine the movement phase of the object for at least one of the plurality of sequentially produced images in the series of images by applying a Hilbert transformation to the signal; and
   an x-ray beam source and an x-ray detector configured to produce the series of images of the object.

24. The imaging device as claimed in claim 23, wherein the computer unit is further configured to:
   assign the determined movement phase to images in the series of images; and
   reconstruct an image of the object based on the assignment of the determined movement phase.

25. A computer readable program product having machine-readable instructions executable on a computer unit stored thereon, the instructions comprising:
   providing a plurality of sequentially produced images in a series of images of a moving object;
   registering different images in the series of images;
   determining a deformation that has occurred between the registered images;
   forming a signal indicative of the deformation between the registered images; and
   determining a movement phase of the moving object for at least one image in the series of images using a Hilbert transformation on the signal.

* * * * *